United States Patent [19]

Holick

[11] 4,338,293

[45] Jul. 6, 1982

[54] SUNSCREENING AGENT

[75] Inventor: Michael F. Holick, Sudbury, Mass.

[73] Assignee: Massachusetts General Hospital, Boston, Mass.

[21] Appl. No.: 238,075

[22] Filed: Feb. 25, 1981

[51] Int. Cl.³ .................................................. A61K 7/42
[52] U.S. Cl. ....................................................... 424/59
[58] Field of Search ............................ 260/397.2; 424/59

[56] References Cited

U.S. PATENT DOCUMENTS 3,488,733  1/1970  Diassi et al. ........................... 424/59
3,697,559  10/1972  DeLuca et al. .................... 260/397.2
3,751,563  8/1973  Richardson ............................ 424/59
4,098,881  7/1978  Majeti .................................... 424/59

Primary Examiner—Elbert L. Roberts
Attorney, Agent, or Firm—Oblon, Fisher, Spivak, McClelland & Maier

[57] ABSTRACT

A sunscreening composition which comprises a sunscreening amount of a $\Delta^{5,7}$ steroidal diene and a topical carrier, with the proviso that the $\Delta^{5,7}$ steroidal diene is not a precursor to a biologically active vitamin D compound.

11 Claims, 2 Drawing Figures

SUNSCREENING AGENT

BACKGROUND OF THE INVENTION

1. Field of the Invention

The present invention relates to sunscreen compositions and methods for protecting the skin from ultraviolet radiation.

2. Description of the Prior Art

Sunscreens are used in the prevention of sunburns. Acute cutaneous responses to ultraviolet light (UVL) range from sunburn and suntan to photosensitivity states. The ultraviolet spectrum at the earth's surface consists of wavelengths from 290 nm to 400 nm. Normal sunburn and subsequent tanning result from UVB radiation (290 to 320 nm); UVA or long ultraviolet rays (320 to 400 nm) causes immediate pigment darkening but in high enough doses can induce new pigment formation. UVA is also responsible for most photosensitivity reactions. UVC (less than 290 nm) is not found at the earth's surface, it is filtered out by the atmosphere.

There is strong evidence that UVB is the major cause of aging of the skin and the development of cutaneous carcinoma. Evidence has been presented linking UVL exposure with skin cancer.

The most widely used chemical sunscreening agents are chemicals that protect the skin by absorbing UVL, and then dissipating the energy in a harmless manner. These compounds must (1) filter UVL between 290 and 320 m; (2) be stable; (3) be non-toxic; (4) be non-sensitizing; and (5) be non-volatile.

The major chemical sunscreens in use today are para-aminobenzoic acid derivatives, cinnamates, anthranilates, and benzophenones. (The previous discussion is essentially adopted from "Topical Photoprotective Agents", Algra, R. J. et al, International Journal of Dermatology, 17:628–634 (1978)).

Although these chemical agents are in wide use, most of them exhibit unwanted side problems. p-aminobenzoic acid for example may stain clothing yellow, especially after its exposure to the sun. Furthermore, allergic contact and photocontact dermatitis to p-aminobenzoic acid and its derivatives have been reported. Patients allergic to benzocaine, procaine, para phenylenediamine and sulfonylamide may have allergic reactions to p-aminobenzoic acid. A patient allergic to thiazide or sulfa drugs may have a reaction to sunscreens containing p-aminobenzoic acid or p-aminobenzoic acid esters. Contact dermatitis also occasionally develops from benzophenones and cinnamates; glyceryl p-aminobenzoic acid seems to be the most common cause. A number of other sunscreens can also cause photocontact dermatitis.

In view of these problems, it would be desirable to use compounds with somewhat decreased side effects. Especially desirable would be compounds belonging to a naturally occurring series, such as steroids.

The use of steroids in sunscreening compositions has been disclosed, mainly as anti-inflammatory additives. (See Algra et al supra, at page 631). Unfortunately, corticosteroids have little effect on sunburn erythema. Although both hydrocortisone and beta methasone-valerate may delay the onset of erythema at one to times the minimal erythema dose, neither is effective with higher doses of ultraviolet light.

Diassi, U.S. Pat. No. 3,542,811 describes 6-halo-6-dehydro-A-norprogesterones as useful for sunscreening. Pike, J. E. et al, U.S. Pat. No. 3,436,388 describe steroid 16-oxopregnan-21-oic acid di substituted amides, suggesting that when used topically they absorb a portion of erythema producing ultraviolet rays, and would thus be useful as ultraviolet screening agents. Pike, U.S. Pat. No. 3,178,459 describes androstano-(16,17-1',2')-benzenes, suggesting that they can be employed effectively as sunburn screens. Pike, U.S. Pat. No. 3,162,631 describes steroid 16$\beta$-hydroxy-21-carboxylic acid $\gamma$-lactones of the pregnane series, and also suggests that they can be used as ultraviolet screens. Diassi et al U.S. Pat. No. 3,488,733 describes the production of 14$\alpha$- and 15$\beta$-oxygenated-16-dehydro steroids of the pregnane series, suggesting that they could be used as sunscreening agents. Finally, Jackson et al U.S. Pat. No. 3,114,757 describes 6-fluorosteroids, also stating that they would be useful as sunscreening agents. None of the steroids described in these references however is a $\Delta^{5,7}$ steroidal diene or $\Delta^{3,5,7}$ steroidal triene.

Leigh, U.S. Pat. No. 3,981,996 describes sunscreening preparations comprising mixtures of vitamins A and D. It should be noted, of course, that vitamin D can be produced from provitamin D (a $\Delta^{5,7}$ steroidal diene) by a sequence of photochemical and thermal isomerization steps.

In addition, Holick, M. F., et al The New England Journal of Medicine, 303:349–354 (1980), have suggested the topical application of 1$\alpha$,25-dihydroxy-7-dehydrocholesterol as being useful to deliver equivalent doses of 1$\alpha$,25-dihydroxyvitamin $D_3$ to patients with impaired vitamin D metabolism. The concept of applying hydroxylated provitamin D's (such as 1,25 dihydroxy-7-dehydrocholesterol) has been incorporated into U.S. Application Serial No. 022,393 filed Mar. 21, 1979 by Holick et al. Furthermore, the concept of adding to opacifying agents nonhydroxylated $\Delta^{5,7}$ steroidal dienes which are precursors of biologically active vitamin D has been incorporated into U.S. Application Ser. No. 193,297, filed Oct. 2, 1980 at the U.S. Patent Office, by Holick. Both of these applications however, relate to the use of precursors of biologically active vitamin D's.

A need therefore continues to exist for sunscreening compositions containing as the active sunscreening agent per se, molecules belonging to a family of naturally occurring compounds such as the steroids.

SUMMARY OF THE INVENTION

It is therefore an object of the invention to provide novel sunscreening compositions.

It is another object of the invention to provide a method of protecting human skin from ultraviolet radiation.

These and other objects of the invention which will hereinafter become more readily apparent, have been attained by providing:

a sunscreening composition which comprises:
  a sunscreening amount of a $\Delta^{5,7}$ steroidal diene together with a topical carrier; with the proviso that said $\Delta^{5,7}$ steroidal diene is not a precursor to a biologically active vitamin D compound.

Another object of the invention has been attained by providing a method of protecting the human skin from ultraviolet radiation which comprises applying to said skin a $\Delta^{5,7}$ steroidal diene with the proviso that said steroidal diene is not a precursor to a biologically active vitamin D compound.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
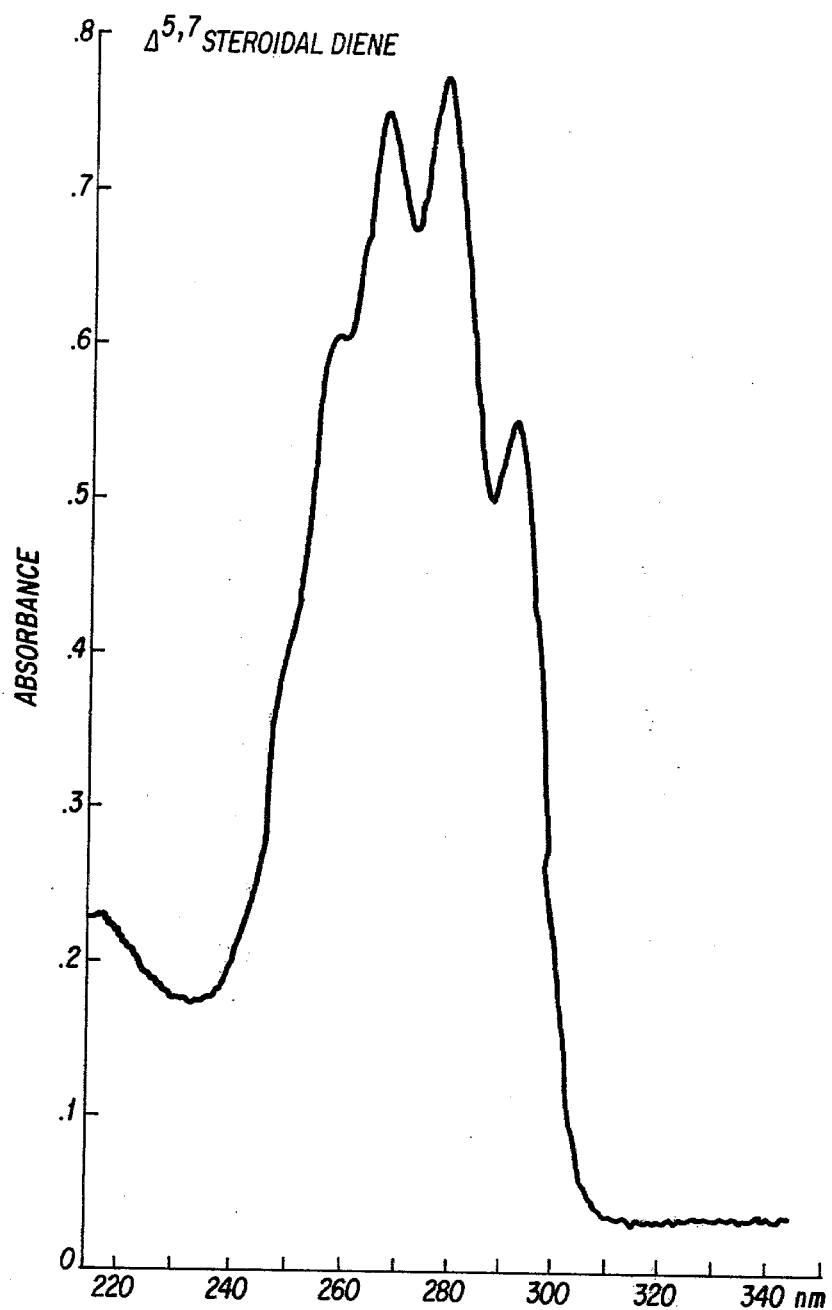
FIG. 1 is the ultraviolet absorption spectrum for a $\Delta^{5,7}$ steroidal diene, specifically 7-dehydrocholesterol.
Figure 2:
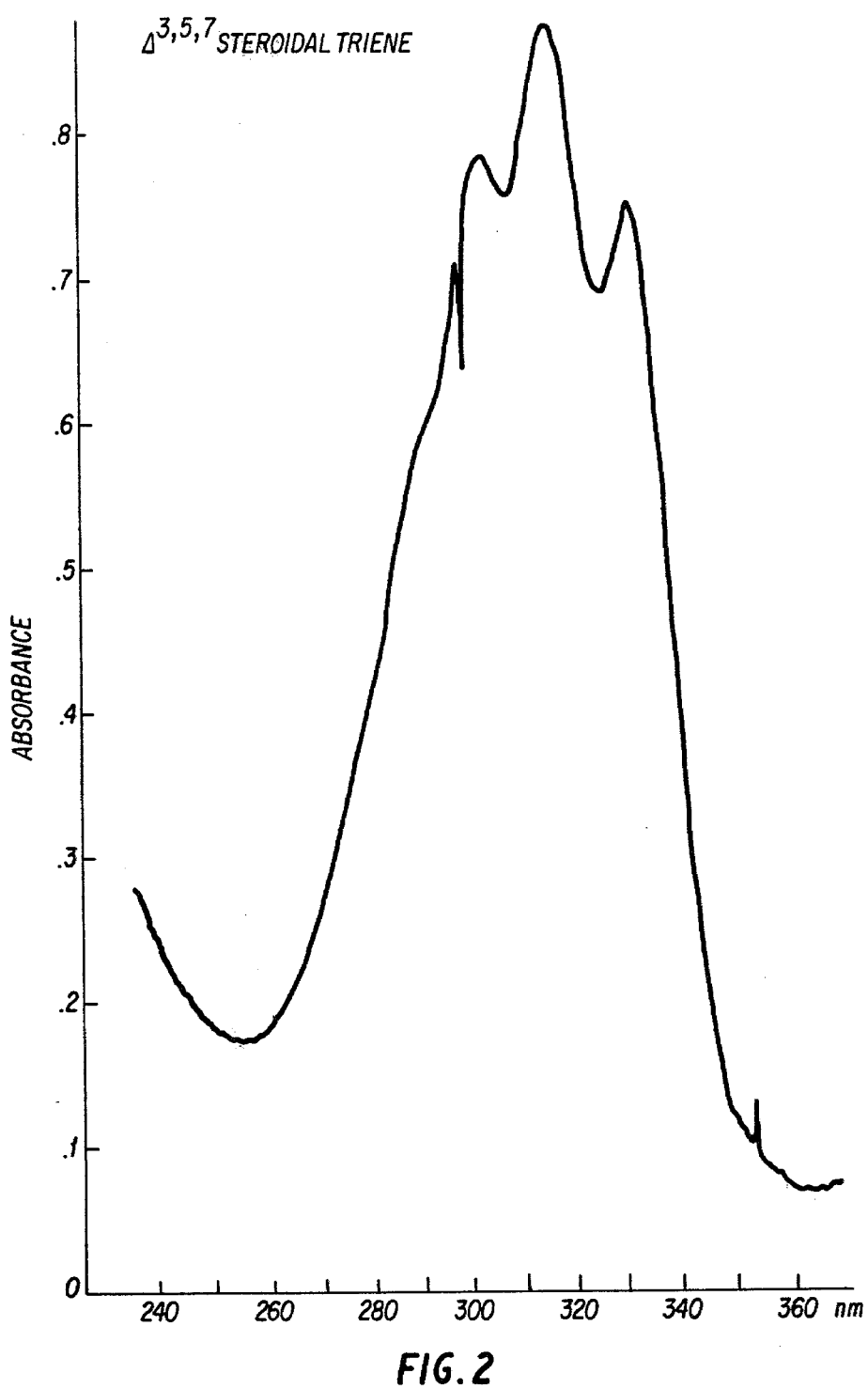
FIG. 2 shows the ultraviolet absorption spectrum of a $\Delta^{3,5,7}$ steroidal triene, specifically cholesta-5,7-diene-3-one enolacetate.

The present inventor has discovered that the spectral characteristics of the ultraviolet absorption of $\Delta^{5,7}$ steroidal dienes render these compounds highly useful as active ingredients for sunscreening compositions. The ultraviolet absorption spectra of $\Delta^{5,7}$ steroidal dienes has $\lambda_{max}$ in the region of 260–300 nm with an extinction coefficient of about 10,000. These spectral characteristics are well suited to block UVB radiation (290–320 nm) which is the cause of normal sunburn. In this respect, particularly preferred $\Delta^{5,7}$ steroids are those which contain an extra double bond at position 3, i.e., $\Delta^{3,5,7}$ steroidal trienes. The ultraviolet absorption spectra of $\Delta^{3,5,7}$ steroidal trienes has a $\lambda_{max}$ in the region of 250–350 nm with maxima around 320 nm. The extinction coefficients range between 14,000 and 20,000. The trienes therefore are not only useful in blocking UVB radiation (290 through 320 nm), but are also ideally suited as UVA sunscreens (320–400 nm), which is responsible for most photosensitivity reactions.

The word "steroid" has a well defined meaning to those skilled in the art. Thus, for example, Morrison and Boyd, "Organic Chemistry", 3rd edition, 1973, at page 514, define a steroid as a molecule having the following formula (given here with the standard ring numbering and lettering system):

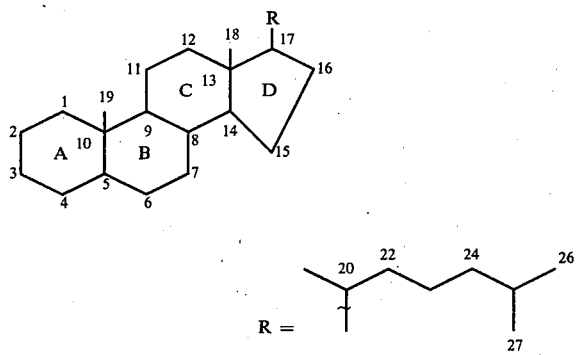

In the present invention, $\Delta^{5,7}$ steroidal dienes are used, having the following generalized formula:

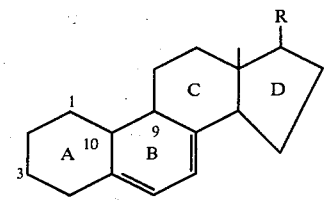

The preferred $\Delta^{3,5,7}$ steroidal trienes have the following generalized formula:

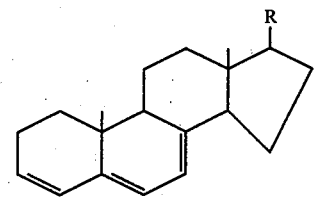

The most preferred compounds of the present invention are $\Delta^{3,5,7}$ steroidal trienes-3-enol-acylates and alkoxylates of the formula:

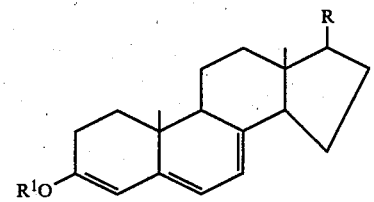

wherein R is as defined above and $R^1$ is substituted or unsubstituted $C_1$–$C_{12}$ alkyl, preferably lower alkyl; or is aryl, such as phenyl, naphthyl, etc.; or $R^1$ is $R^2$-'CO, wherein $R^2$ is $C_1$–$C_{12}$ alkyl, preferably lower alkyl, or $R^2$ is aryl.

The aforementioned dienes and trienes may be substituted or unsubstituted at any position thereof by $C_1$–$C_{20}$ alkyl groups, preferably lower alkyl groups; halogen, such as fluorine, chlorine, bromine, or iodine; hydroxy; alkoxy, preferably lower alkoxy; acyloxy, preferably lower acyloxy; aralkyl; aryl, preferably phenyl or naphthyl; cycloalkyl, such as cyclohexyl, cyclopentyl; amines, preferably lower alkyl secondary or tertiary amines; acylamines; preferably lower alkyl acylamines, carboxylic acid; esters thereof, preferably lower alkyl esters thereof; amides thereof, preferably lower alkyl secondary and tertiary amides thereof; or salts thereof, such as alkyl and metal salts or organic ammonium salts thereof. Any of steroidal rings, A, B, C or D may also be substituted by ketone functionalities; their imines such as hydrazones, phenylhydrazones, and the like; their oximes, alkyl oximes, or hydroxamic acids. When the steroidal rings A, B, C and D are substituted by alkyl or aralkyl, the alkyl groups may be themselves substituted by any of the aforementioned substituents such as halogen, hydroxy, alkoxy, and the like. In general, any substituent which does not interfere with the ultraviolet absorption spectra characteristics of the dienes or trienes of the invention, i.e., substituents which substantially do not have auxochromic or batochromic effects which would shift the ultraviolet spectra away from the UVA and/or UVB regions, are equivalent to those mentioned previously, and therefore acceptable for the compounds of the invention. Substituents which are not conjugated with the diene or triene system are preferred.

One critical proviso for the use of $\Delta^{5,7}$ steroidal dienes in the present invention is that they should not be precursors to a biologically active vitamin D compound, especially to $1\alpha,25$-dihydroxyvitamin $D_3$. $\Delta^{5,7}$ steroidal dienes are photosensitive to ultraviolet radiation, and ring-open at the $C_9$–$C_{10}$ bond. This reaction is well known in the vitamin D field, and is responsible for the photochemical transformation in skin of 7-dehydrocholesterol to previtamin D. (See for example Holick, M. F. et al, Biochemical and Biophysical Research Communications, 76:107–114 (1977) and Holick, M. F. et al, New England Journal of Medicine, 303:349–354 (1980) Holick, M. F. et al, Science, 210:203–205 (1980)). Previtamin D normally undergoes a thermally induced sigmatropic shift in order to be converted to vitamin D. Furthermore, vitamin D is next hydroxylated at positions $1\alpha$ and 25 to yield $1\alpha,25$ dihydroxyvitamin $D_3$, which is the hypocalcemically active metabolite capable of maintaining calcium and phosporous homeostasis. Any $\Delta^{5,7}$ steroidal diene which upon photolysis yields a previtamin D capable of undergoing further thermal rearrangement and hydroxylation to a biologically active vitamin D compound is not included in the present invention. The $\Delta^{5,7}$ steroidal dienes of the present invention, although potentially capable of $C_9$–$C_{10}$ bond cleavage by photolysis, are those wherein either the thermal rearrangement is blocked, or the hydroxylation reactions in liver and kidney at positions $1\alpha$ or 25 are blocked, or both of these mechanisms are blocked. This proviso thus excludes from the steroidal dienes of the present invention compounds such as 7-dehydrocholesterol, or $\Delta^{5,7}$ steroidal dienes having, as their sole substituents, hydroxyl groups at positions 1; 1, 25; 1, 24, 25; and 1, 25, 26.

$\Delta^{3,5,7}$ steroidal trienes are inherently not precursors of any biologically active vitamin D compound. Thus any $\Delta^{3,5,7}$ steroidal triene can be used in the present invention.

Specific $\Delta^{5,7}$ steroidal dienes useful in the invention are:
3-chloro-cholesta-5-7-diene
3-bromo-cholesta-5,7-diene
3-deoxy-cholesta-5,7-diene
3-deoxy-ergosterol
3-chloro-ergosterol
3-bromo-ergosterol
3-methoxy-cholesta-5,7-diene
3-ethoxy-cholesta-5,7-diene
3-methoxy-ergosterol
3-ethoxy-ergosterol
A-homo-cholesta-5,7-diene
A-homo-ergosta-5,7,22-tetraene
$\Delta^{5,7}$-pregnenalone
$\Delta^{5,7}$-pregnenalol
27,26,25,24-tetranor-cholesta-5,7-diene and other side chain derivatives.

Among the $\Delta^{3,5,7}$ steroidal trienes can be listed:
3-acetoxy-3,5,7,22-ergosta-tetraene,
3-acetoxy-3,5,7-cholestatriene,
3-deoxy-3,5,7,22-ergosta-tetraene,
3-deoxy-3,5,7-cholestatriene
27,26,25,24,23,22-hexanor-3-acetoxy-3,5,7-cholestatriene
27,26,25,24,23,22-hexanor-21-hydroxy (methoxy) or (acetoxy)--3-acetoxy or (methoxy)-cholesta-3,5,7-cholestatriene The general and specific synthesis of $\Delta^{5,7}$ steroidal dienes is well known in the art. See for example Dauben et al, Journal of the American Chemical Society 75:3255–3258 (1953); Dauben ibid, 73:4496 (1951); Bernstein et al, ibid, 75:1480–1481 (1953); or Dauben et al U.S. Pat. No. 2,926,163. This patent teaches specifically the preparation of $\Delta^{5,7}$ 3-hydroxy steroids. See also Semmler, E. J. et al, Tetrahedron Letters, 40:4147–4150 (1972); Lam, H. Y. et al, Biochemstry 12:4851–4855 (1973); Barton, D. H. R. et al, Journal of the American Chemical Society, 95:2748–2749 (1973); Holick, M. F. et al Journal of Biological Chemistry, 250:226–230, (1975); Salmond, W. D. "Vitamin D, Basic Research and its Clinical Application", Proceedings of the Fourth Workshop on Vitamin D, Berlin, West Germany, February, 1979, Norman A. W., editors, New York, 1979, pp. 25–31; Ikekawa N. et al, ibid, pp. 13–19; Salmond, W. D. ibid pp. 62–70; Crump, D. R. et al, Journal of the Chemical Society, Perkin I, 1973, 2731–2733.

The synthesis of $\Delta^{3,5,7}$ steroidal trienes, especially the synthesis of the preferred ones carrying an enol acylate derived from a hydroxy group at position 3, can generally be carried out by oxidizing 3-hydroxy-$\Delta^{5,7}$ steroidal dienes to give a 3-keto-$\Delta^{4,7}$ trianone. Treatment of this ketone with an anhydride such as acetic anhydride or benzoic anhydride yields the $\Delta^{3,5,7}$ enol acylate. This sequence of reactions is shown in Scheme 1.

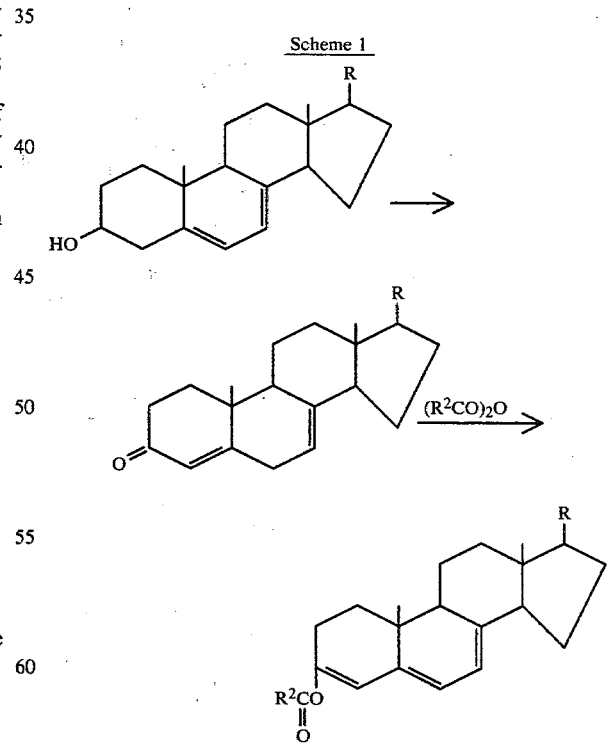

Scheme 1

Treatment of the enol acylate with alcohol $R^1OH$ in the presence of $Hg(OAc)_2$ yields the enol ether (Buehler, C. A. and Pearson, D. E., Survey of Organic Synthesis, Vol. I, p. 305, 1970; John Wiley & Sons):

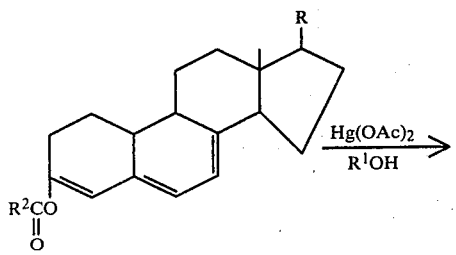

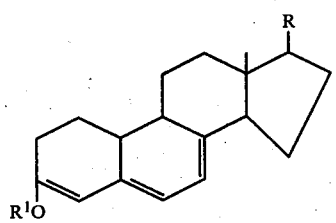

This sequence of reactions and a number of examples can be found in Heilbron, I. M. et al, Journal of the Chemical Society, 1938, 869–876. Preparation of other steroidal trienes of this family can be carried out in an analogous manner.

Other references to synthetic methods of preparing trienes are:

Shepard et al, J. Am. Chem. Soc. 77, 1212, 1955; Holick et al, Biochemistry 19, 3933–3937, 1980; Jones et al, Biochemistry 14, 1250–1256, 1975;

Other references for enol acetate and enol ether formation are:

Cooper, D. J. and Owen, L. N., J. Chem. Soc. (c) 533, 1966; Bedoulian, P. Z., Am. Soc. 67, 1430, 1945; Chamberlin, E. M. and Chemerda, J. M., J. Am. Chem. Soc., 77, 1222, 1959; Deghenghi, R. and Engel, C. R., J. Am. Chem. Soc. 82, 3201, 1960; Fried, J. H., Nutlie, A. N. and Arth, G. E., J. Org. Chem., 26, 976, 1955; Bernstein, S., Heller, M. and Stolar S. M., J. Am. Chem. Soc. 77, 5327, 1955; Billotti, R., Djerassi, C. and Ringold, H. J., J. Am. Chem. Soc. 81, 4566, 1959;

Other references for Enol ethers are:

Nussbaum, A. L., Yuan, E., Dincer, D. and Oliveto, E. P., J. Org. Chem., 26, 3925, 1961; Bernstein, S., Lenhard, R. H. and Williams, J. H., J. Org. Chem. 27, 668, 1962; Gardi, R., Vitali, R. and Ercoli, A., J. Org. Chem., 27, 668, 1962;

A general reference for steroid derivatization is:

"Steroid Reactions: An outline for Organic Chemists", Ed. Carl Djerassi, Holden-Day, Inc., San Francisco, 1963.

The sunscreening compositions of the invention require a topical, cosmetologically inert carrier in addition to the sunscreening compound. This carrier may be a solvent such as water, glycerol, alcohol, propylene glycol, fatty alcohols, triglycerides, fatty acid esters or mineral oils. Other possible carriers are liquid petrolatum (nujol), isopropyl palmitate polyethylene glycol, ethanol 95%, polyoxyethylene monolaurate 5% in water, sodium lauryl sulfate 5% in water. Any other normally used sunscreen carriers can of course be used in the present invention. Other materials, such as antioxidants, humectants, viscosity stabilizers and the like may be added if necessary. The dienes and trienes of the present invention may be present in an amount sufficient to provide sunscreening action.

The sunscreening compositions can be liquids or pastes of different viscosity. When a composition is liquid it may contain 0.01 to 99.9% of the steroids, with the remainder being carrier, antioxidant, emulsifiers and the like. Preferably, the range is 0.05–50% by weight. When the composition is an ointment or cream or paste, the $\Delta^{5,7}$ steroids are present in 0.01–99.9% by weight, preferably, 0.05–50%.

The sunscreening compositions of the invention can be applied topically in the same manner as other normally used sunscreening compositions. At least one microgram, preferably at least 100 micrograms of the steroidal dienes are administered to the skin per square centimeter. In general, no more than about 100 mg/cm² should be necessary.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A sunscreen composition which comprises a sunscreening amount of a substituted or unsubstituted $\Delta^{5,7}$ steroidal diene capable of blocking UVB radiation and having the formula

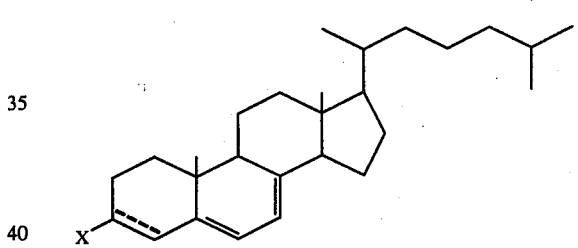

wherein X is H or R¹O; where R¹ is C₁–C₁₂ alkyl, aryl or R¹ is R²CO, where R² is C₁–C₁₂ alkyl or aryl; and a topical carrier; with a proviso that said $\Delta^{5,7}$ steroidal diene is not a precursor to a biologically active vitamin D compound.

2. The composition of claim 1 wherein said $\Delta^{5,7}$ steroidal diene contains a double bond at position 3-thereof.

3. The composition of claim 2 wherein said diene is a 3-deoxy diene.

4. The composition of claim 2 wherein said diene is a 3-enol acylated steroid.

5. The composition of claim 2 wherein said diene is a 3-enol ether steroid.

6. The composition of claim 1 wherein said biologically active vitamin D compound is 1 α, 25 -dihydroxyvitamin D₃.

7. A method for protecting the human skin from ultraviolet radiation which comprises applying to said skin a substituted or unsubstituted $\Delta^{5,7}$ steroidal diene capable of blocking UVB radiation and having the formula

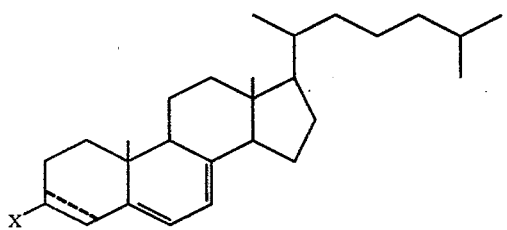

wherein X is H or $R^1O$, where $R^1$ is $C_1$–$C_{12}$ alkyl, aryl or $R^1$ is $R^2CO$, where $R^2$ is $C_1$–$C_{12}$ alkyl or aryl; with the proviso that said diene is not a precursor to a biologically active vitamin D compound.

8. The method of claim 7 wherein said $\Delta^{5,7}$ steroidal diene contains a double bond at position 3-thereof.

9. The method of claim 8, wherein said diene is a 3-deoxy diene.

10. The method of claim 8 wherein said $\Delta^{5,7}$ steroidal diene is a 3-enol acylated steroid.

11. The method of claim 8 wherein said $\Delta^{5,7}$ steroidal diene is a 3-enol ether steroid.

* * * * *